United States Patent [19]

Büchel et al.

[11] Patent Number: 4,659,723

[45] Date of Patent: Apr. 21, 1987

[54] SUBSTITUTED AZOLYLALKYL PYRIDINYL ETHERS

[75] Inventors: Karl H. Büchel, Burscheid; Udo Kraatz, Leverkusen; Jörg Stetter, Wuppertal; Paul Reinecke, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 798,525

[22] Filed: Nov. 15, 1985

[30] Foreign Application Priority Data

Nov. 29, 1984 [DE] Fed. Rep. of Germany ....... 3443597

[51] Int. Cl.$^4$ ................... C07D 401/12; A01N 43/40; A01N 43/50
[52] U.S. Cl. ..................................... 514/341; 546/278
[58] Field of Search ................. 546/276, 278; 514/341

[56] References Cited

U.S. PATENT DOCUMENTS

| | | | |
|---|---|---|---|
| 4,330,547 | 5/1982 | Kraatz et al. | 546/276 |
| 4,396,624 | 8/1983 | Stetter et al. | 546/276 |
| 4,399,143 | 8/1983 | Yokomichi et al. | 546/276 |
| 4,411,687 | 10/1983 | Zech et al. | 546/276 |
| 4,427,672 | 1/1984 | Kraatz et al. | 546/276 |

*Primary Examiner*—John M. Ford
*Attorney, Agent, or Firm*—Sprung Horn Kramer & Woods

[57] ABSTRACT

Novel substituted azolylalkyl pyridinyl ethers of the formula

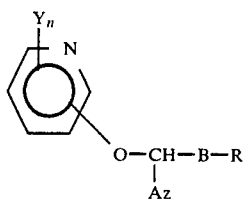

in which
Az represents 1,2,4-triazolyl or imidazolyl,
B represents the keto or the CH(OH) group,
Y represents halogen, alkyl, alkoxy, alkylthio, alkylsulphonyl, halogenoalkyl, nitro, cyano, alkoxycarbonyl or optionally substituted phenyl
R represents optionally substituted aryl or the groupings

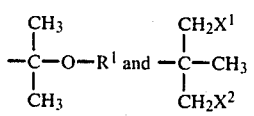

wherein
$R^1$ represents optionally substituted aryl,
$X^1$ represents halogen and
$X^2$ represents hydrogen and halogen, and
n represents the numbers 0, 1, 2 and 3, and their acid addition salts and metal salt complexes, are outstandingly effective as fungicides.

8 Claims, No Drawings

SUBSTITUTED AZOLYLALKYL PYRIDINYL ETHERS

The present invention relates to new substituted azolylalkyl pyridinyl ethers, to fungicidal compositions containing them and to their use as fungicides.

It has been disclosed that azolylalkyl pyridinyl ethers have generally good fungicidal properties (in this context, see German Offenlegungsschriften (German Published Specifications Nos.) 2,756,269, 3,000,244 and 3,028,669. However, the action of these compounds is not always completely satisfactory, particularly when small amounts and concentrations are used.

The present invention now provides, as new compounds, the substituted azolylalkyl pyridinyl ethers of the formula

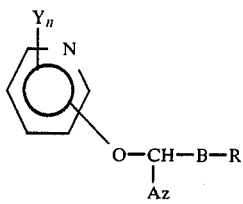

in which
Az represents 1,2,4-triazolyl or imidazolyl,
B represents the keto or the CH(OH) group,
Y represents halogen, alkyl, alkoxy, alkylthio, alkylsulphonyl, halogenoalkyl, nitro, cyano, alkoxycarbonyl or optionally substituted phenyl, R represents optionally substituted aryl or the groupings

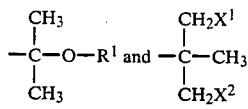

wherein
$R^1$ represents optionally substituted aryl,
$X^1$ represents halogen and
$X^2$ represents hydrogen and halogen, and
n represents the numbers 0, 1, 2 and 3,
and their acid addition salts and metal salt complexes.

The substituted azolylalkyl pyridinyl ethers of the general formula (I)

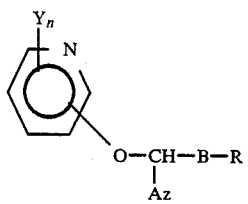

in which
Az represents 1,2,4-triazolyl or imidazolyl,
B represents the keto or the CH(OH) group,
Y represents halogen, alkyl, alkoxy, alkylthio, alkylsulphonyl, halogenoalkyl, nitro, cyano, alkoxycarbonyl or optionally substituted phenyl R represents optionally substituted aryl or the groupings

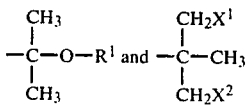

wherein
$R^1$ represents optionally substituted aryl,
$X^1$ represents halogen and
$X^2$ represents hydrogen and halogen, and
n represents the numbers 0, 1, 2 and 3,
are obtained when halogeno ether-ketones of the formula (II)

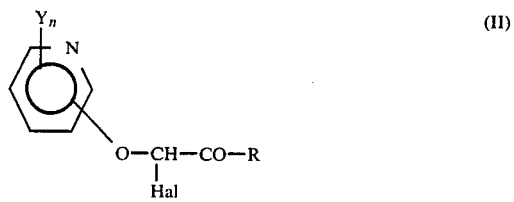

in which
Hal represents halogen, preferably chlorine or bromine, and
Y, R and the index n have the meaning given above,
are reacted with a compound of the formula (III)

in which
Az has the meaning given above,
in the presence of a diluent and in the presence of an acid-binding agent, and, if appropriate, the resulting keto derivatives of the formula (Ia)

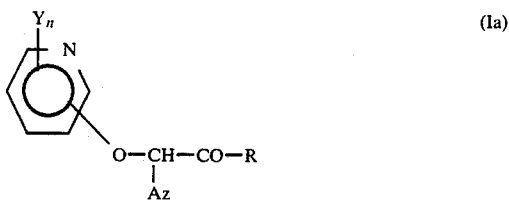

in which
Y, R, Az and the index n have the meaning given above,
are reduced in a customary manner by known methods.

The compounds of the formula (I) which are obtained in this manner can, if appropriate, then be subjected to an addition reaction with an acid or a metal salt. In some cases, it proves to be advantageous to obtain the compounds of the formula (I) in pure form via their salts.

The new substituted azolylalkyl pyridinyl ethers of the formula (I), their acid addition salts and metal salt complexes possess powerful fungicidal properties. In this contex, the compounds according to the invention surprisingly exhibit a better fungicidal action than the azolyl pyridinyl ethers which are known from the prior art and are similar compounds chemically and in terms of their action.

Furthermore, the new compounds of the formula (I) are interesting intermediate products for the preparation of further active compounds for plant protection. Thus, functional derivatives of the keto group, such as, for example, oximes and oxime-ethers, hydrazones and ketals, can be obtained by appropriate reaction. Moreover, the compounds of the formula (I) can be converted in a customary manner to the corresponding ethers at the hydroxyl group, or acyl or carbamoyl derivatives can be obtained by reaction with, for example, acyl halides or carbamoyl chlorides in a manner which is known in principle.

The substances according to the invention thus represent a substantial enrichment of the art.

Formula (I) gives a general definition of the substituted azolylalkyl pyridinyl ethers according to the invention. Preferred compounds of the formula (I) are those in which Y represents halogen, or alkyl, alkoxy, alkylthio or alkylsulphonyl, each having 1 to 4 carbon atoms, or halogenoalkyl having 1 to 4 carbon atoms and 1 to 5 identical or different halogen atoms, or nitro, cyano, alkoxycarbonyl having 1 to 4 carbon atoms in the alkyl part, or phenyl which is optionally substituted by halogen, R represents optionally substituted phenyl, halogen, and alkyl, alkoxy and alkylthio, each having 1 to 4 carbon atoms, and halogenoalkyl, halogenoalkoxy and halogenoalkylthio, each having 1 to 4 carbon atoms and 1 to 5 identical or different halogen atoms, and nitro, cyano, alkoxycarbonyl having 1 to 4 carbon atoms in the alkyl part, and phenyl which is optionally substituted by halogen being mentioned as substituents, and furthermore represents the groupings

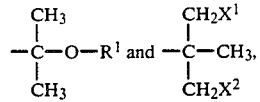

wherein
R¹ represents phenyl which can optionally be substituted by the phenyl substituents mentioned above in the case of R,
X¹ represents halogen and
X² represents hydrogen and halogen, and
Az, B and the index n have the meanings stated in the definition of the invention.

Particularly preferred compounds of the formula (I) are those in which

Y represents fluorine, chlorine, bromine, methyl, isopropyl, tert.-butyl, methoxy, methylthio, methylsulphonyl, trifluoromethyl, nitro, cyano, methoxycarbonyl, ethoxycarbonyl and represents phenyl which is optionally monosubstituted to trisubstituted by fluorine or chlorine, n represents the numbers 0, 1 and 2, R represents phenyl which can optionally be monosubstituted to trisubstituted by substituents selected from fluorine, chlorine, methyl, ethyl, isopropyl, tert.-butyl, methoxy, methylthio, trifluoromethyl, trifluoromethoxy, trifluoromethylthio, nitro, cyano and phenyl which is optionally substituted by fluorine and chlorine, and furthermore represents the groupings

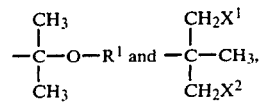

in which
R¹ represents phenyl which can optionally be monosubstituted to trisubstituted by the phenyl substituents mentioned above in the case of R,
X¹ represents fluorine or chlorine and
X² represents hydrogen, fluorine or chlorine, and
Az and B have the meaning given in the definition of the invention.

If, for example, 1-bromo-3-(4-chlorophenoxy)-1-(2-chloropyrid-6-yloxy)-3-methyl-butan-2-one and 1,2,4-triazole are used as starting materials for the preparation of the substituted azolylalkyl pyridinyl ethers according to the invention, only the reaction can be represented by the following equation:

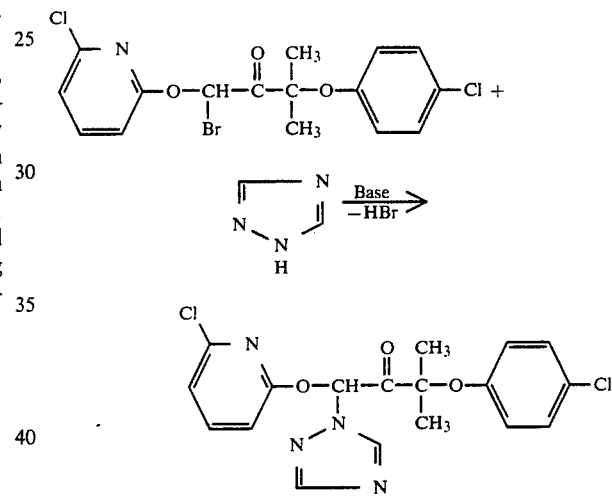

If, furthermore, sodium boranate is used as a reducing agent for the reduction of the 1-(2-chloropyrid-6-yloxy)-3-methyl-3-(4-chlorophenoxy)-1-(1,2,4-triazol-1-yl)-butan-2-one obtained in the above example, the course of the reaction can be represented by the following equation:

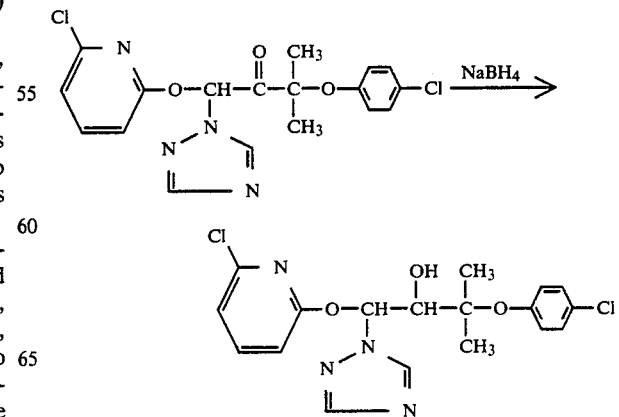

Formula (II) gives a general definition of the halogeno ether-ketones to be used as starting materials in carrying out the process according to the invention for the preparation of the compounds of the general formula (I). In this formula, R, Y and the index n preferably represent those radicals which have already been mentioned in connection with the description of the substances according to the invention, of the formula (I), as being preferred for these substituents.

The halogen ether-ketones of the formula (II) were hitherto unknown. They can however be obtained by known processes, by reacting, for example, known hydroxypyridines of the formula (IV)

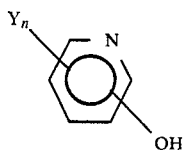 (IV)

in which
Y and the index n have the meaning given above, with a halogenoketone of the formula (V)

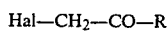 (V)

in which
Hal represents chlorine or bromine and
R has the meaning given above,
in a suitable solvent, such as, for example, acetone, acetonitrile or dioxane, in the temperature range between +20° and 100° C.

The active hydrogen atom still remaining is then exchanged for halogen in a customary manner (see the preparation examples). The halogeno ether-ketones of the formula (II) can, if required, be directly reacted further, without isolation.

Another variant of the abovementioned synthesis is suitable for the preparation of substituted azolylalkyl pyridinyl ethers according to the invention, of the general formula (I): thus, azolyl halogenoketones of the general formula (VI)

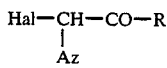 (VI)

in which
Hal represents chlorine or bromine and
R and Az have the meaning given above,
can be reacted with the hydroxypyridines denoted above, of the general formula (IV), in a suitable diluent, such as, for example, acetonitrile, acetone or dioxane, in the temperature range between +20° and 100° C.

The azolyl halogenoketones of the formula (VI) were hitherto unknown. However, they can be obtained by known processes, by reacting an azole of the formula (III) with a halogenoketone of the formula (V) in a suitable diluent, such as, for example, acetonitrile, acetone or dioxane, in the temperature range between +20° and 100° C., and then halogenating the product to give the compounds of the formula (VI). The latter can, if required, be directly reacted further, without isolation.

Suitable diluents for the reaction, according to the invention, of the halogeno ether-ketones of the formula (II) with the azoles of the formula (III) are inert organic solvents.

These preferably include ketones, such as diethyl ketone and in particular acetone and methyl ethyl ketone; nitriles, such as propionitrile, in particular acetonitrile; alcohols, such as ethanol or isopropanol; ethers, such as tetrahydrofuran or dioxane; benzene; toluene; formamides, such as, in particular, dimethylformamide; and halogenated hydrocarbons.

The reaction according to the invention is carried out in the presence of an acid-binding agent. All customarily usable inorganic or organic acid-binding agents can be added, such as alkali metal carbonates, for example sodium carbonate, potassium carbonate and sodium bicarbonate, or such as lower tertiary alkylamines, cycloalkylamines or aralkylamines, for example triethylamine, N,N-dimethylcyclohexylamine, dicyclohexylamine or N,N-dimethylbenzylamine, and furthermore pyridine and diazabicyclooctane. An appropriate excess of azole is preferably used.

The reaction temperatures can be varied within a relatively wide range. In general, the reaction is carried out at between about 20° and about 150° C., preferably at 60° to 120° C. In the presence of a solvent, the reaction is advantageously carried out at the boiling point of the particular solvent.

In carrying out the process according to the invention, 2 to 4 mol of azole and 1 to 4 mol of acid-binding agent are preferably employed per mol of the compound of formula (II). To isolate the compounds of the formula (I), the solvent is distilled off, the residue is taken up with an organic solvent, and the solution is washed with water. The organic phase is dried over sodium sulphate and freed from the solvent in vacuo. The residue is purified by distillation of recrystallisation, or salt formation and recrystallisation.

The reduction, according to the invention, of the compounds of the formula (Ia) is carried out in a customary manner, such as, for example, by reaction with complex hydrides, if appropriate in the presence of a diluent, or by reaction with aluminium isopropylate in the presence of a diluent.

If complex hydrides are employed, suitable diluents for the reaction according to the invention are polar organic solvents. These preferably include alcohols, such as methanol, ethanol, butanol and isopropanol, and ethers, such as diethyl ether or tetrahydrofuran. The reaction is carried out in general at 0° to 30° C., preferably at 0° to 20° C. For this purpose, about 1 mol of a complex hydride, such as sodium borohydride or lithium alanate, is employed per mol of the ketone of the formula (Ia). To isolate the reduced compounds, the residue is taken up in dilute hydrochloric acid, the solution is then rendered alkaline, and extraction is carried out using an organic solvent. Further working-up is effected in a customary manner.

If aluminium isopropylate is employed, preferred diluents for the reaction according to the invention are alcohols, such as isopropanol, or inert hydrocarbons, such as benzene. The reaction temperatures can once again be varied within a relatively wide range; in general, the reaction is carried out at between 20° and 120° C., preferably at 50° to 100° C.

To carry out the reaction, about 0.3 to 2 mol of aluminium isopropylate are employed per mol of the ketone of the formula (Ia). To isolate the reduced compounds, the excess solvent is removed in vacuo, and the aluminium compounds formed are decomposed with dilute sulphuric acid or sodium hydroxide solution. Further working-up is effected in a customary manner.

Preferred acids for the preparation of physiologically tolerated acid addition salts of the compounds of the formula (I) are the following acids: hydrohalic acids, such as, for example, hydrochloric acid and hydrobromic acid, in particular hydrochloric acid, and furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and naphthalene-1,5-disulphonic acid. The acid addition salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtration, and, if appropriate, purified by washing with an inert organic solvent.

Preferred salts for the preparation of a metal salt complexes of the compounds of the formula (I) are salts of metals of main groups II to IV and of subgroups I and II and IV to VIII, copper, zinc, manganese, magnesium, tin, iron and nickel being mentioned as examples. Suitable anions of the salts are those which are preferably derived from the following acids: hydrohalic acids, such as, for example, hydrochloric acid and hydrobromic acid, and furthermore phosphoric acid, nitric acid and sulphuric acid.

The metal salt complexes of compounds of the formula (I) can be obtained in a simple manner by customary processes, for example by dissolving the metal salt in alcohol, for example ethanol, and adding the solution to the compound of the formula (I). Metal salt complexes can be isolated in a customary manner, for example by filtration, and, if appropriate, be purified by recrystallisation.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with good success for combating diseases in cereal cultivation, for example against *Leptosphaeria nodorum, Cochliobolus sativus* and *Pyrenophora teres,* and against mildew and rust in cereals. In rice cultivation, the active compounds can be employed against *Pellicularia oryzae* and *Pellicularia sasakii.* In fruit cultivation, the active compounds according to the invention can be employed against powdery mildew fungi, such as *Podosphaera leucotricha,* and against scab fungi.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellants, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomising, misting, vaporising, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogramme of seed, preferably 0.01 to 10 g are generally required.

For the treatment of soil, active compound concentrations of 0.0001 to 0.1% by weight, preferably 0.0001 to 0.02% by weight, are required at the place of action.

PREPARATION EXAMPLES

Example 1

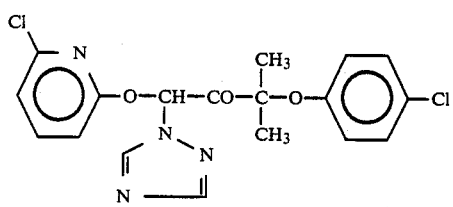

22 g (0.0052 mol) of 1-bromo-1-(2-chloropyridyl-6-oxy)-3-(4-chlorophenoxy)-3-methyl-butan-2-one are dissolved in 150 ml of acetonitrile, and 10.5 g (0.15 mol) of 1,2,4-triazole are added. The mixture is heated at the boil for three hours. Thereafter, the solvent is removed in vacuo, the residue is partitioned between methylene chloride and water, and the organic phase is then separated off, dried and evaporated down. The product which remains behind is chromatographed over silica gel in chloroform/ethyl acetate (4:1) for further purification. 4.8 g (that is 24% of theory) of 1-(2-chloropyrid-6-yl-oxy)-3-(4-chlorophenoxy)-3-methyl-1-(1,2,4-triazol-1-yl)-butan-2-one of melting point 100° C. (from methanol) are obtained.

Precursor:

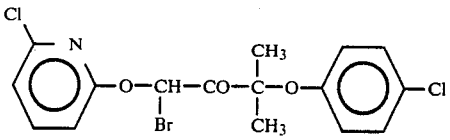

17.8 g (0.1 mol) of N-bromo-succinamide are added to 34 g (0.1 mol) of 3-methyl-1-(2-chloropyrid-6-yloxy)-3-(4-chlorophenoxy)-butan-2-one in 200 ml of carbon tetrachloride, and the mixture is heated at the boil for several hours while being exposed to UV radiation, until all of the N-bromo-succinimide has been converted. The mixture is filtered, and the solution is evaporated down in vacuo. The crude product is used for the reaction stated in Example 1, without further isolation.

Starting material:

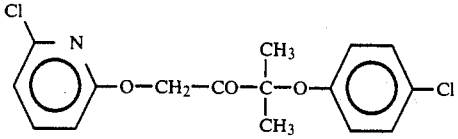

35 g (0.12 mol) of 1-bromo-3-(4-chlorophenoxy)-3-methylbutyl-2-one (see the data in EP-A No. 0 054 865) are heated at the boil for three hours with 16 g (0.12 mol) of 6-chloro-2-hydroxy-pyridine and 28 g (0.2 mol) of potassium carbonate in 300 ml of acetone.

The mixture is then poured into water, the product is extracted with methylene chloride, and the organic phase is evaporated down. The oil which remains is chromatographed over silica gel, in chloroform. 34 g (that is 83% of theory) of 3-(4-chlorophenoxy)-1-(2-chloropyrid-6-yloxy)-3-methyl-butan-2-one are obtained as a clear oil.

Example 1a (For structural formula, see Example 1)

Variant of the preparation process described in Example 1

12.8 g (approx. 4.2 ml, that is 0.08 mol) of bromine are added dropwise to 22.4 g (0.08 mol) of 3-(4-chlorophenoxy)-3-methyl-1-(1,2,4-triazol-1-yl)-butan-2-one in 100 ml of glacial acetic acid at 50° C., while stirring. Thereafter, stirring is continued until the mixture has become completely decolourised (approx. 20 minutes), the mixture is poured into water and extracted with methylene chloride, and the organic phase is washed with sodium bicarbonate until it gives a neutral reaction. Thereafter, the solvent is removed in vacuo, and the residue is dissolved in 100 ml of acetonitrile. A homogeneous solution of 11.6 g (0.1 mol) of chloropyridine and 16 ml (0.1 mol) of triethylamine is added, all at once, to the stirred solution. When the exothermic reaction has died down, the mixture is kept at the boil for a further 30 minutes and then poured into water and extracted with methylene chloride. The organic phase is washed twice with dilute sodium hydroxide solution, and freed from the solvent, and the oil which remains is recrystallised from a small amount of methanol. 12.4 g (that is 31% of theory) of 1-(2-chloropyrid-6-yloxy)-3-(4-chlorophenoxy)-3-methyl-1-(1,2,4-triazol-1-yl)-butan-2-one of melting point 101° C. are obtained.

Example 2

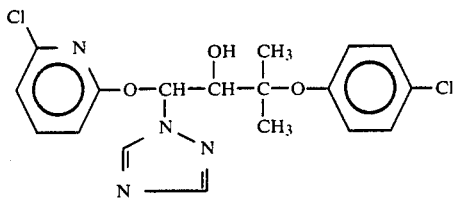

1 g (0.025 mol) of sodium boronate is added to 14.4 g (0.035 mol) of 1-(2-chloropyrid-6-yloxy)-3-(4-chlorophenoxy)-3-methyl-1-(1,2,4-triazol-1-yl)-butan-2-one (see Example 1) in 100 ml of methanol, and the mixture is stirred at 20° C. for one hour. The solvent is removed in a rotary evaporator, and the residue is partitioned between methylene chloride and water. The organic phase is separated off, washed with water and freed from the solvent. 12.4 g (that is 87% of theory) of 1-(2-chloropyrid-6-yloxy)-3-(4-chlorophenoxy)-3-methyl-1-(1,2,4-triazol-1-yl)-butan-2-ol.

The following compounds of the general formula (Ib)

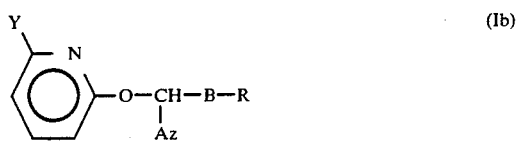

are obtained in a manner corresponding to that indicated in Examples 1 and 2:

| Example No. | Y | Az | B | R | m.p. (°C.) |
|---|---|---|---|---|---|
| 3 | Cl | -N⟨triazole⟩ | CO | -C(CH₃)₂-O-C₆H₄-F | 118 |
| 4 | Cl | -N⟨triazole⟩ | CO | -C(CH₃)₂-O-C₆H₄-Cl | resin |
| 5 | Cl | -N⟨triazole⟩ | CO | -C₆H₄-Cl | 133 |
| 6 | Cl | -N⟨triazole⟩ | CO | -C₆H₄-C₆H₅ | 162 |
| 7 | F | -N⟨triazole⟩ | CO | -C₆H₄-Cl | resin |
| 8 | Cl | -N⟨triazole⟩ | CO | -C(CH₃)₂-CH₂F | 86 |
| 9 | F | -N⟨triazole⟩ | CO | -C(CH₃)₂-CH₂F | 44–46 |

-continued

| Example No. | Y | Az | B | R | m.p. (°C.) |
|---|---|---|---|---|---|
| 10 | Cl | imidazol-1-yl | CO | -C(CH$_2$F)(CH$_3$)(CH$_2$F) | 70 |
| 11 | F | imidazol-1-yl | CO | -C(CH$_2$F)(CH$_3$)(CH$_2$F) | resin |
| 12 | Cl | imidazol-1-yl | CO | -C(CH$_3$)(CH$_2$Cl)(CH$_3$) | 83 |
| 13 | F | imidazol-1-yl | CO | -C(CH$_3$)(CH$_2$Cl)(CH$_3$) | 70–75 |
| 14 | Cl | imidazol-1-yl | CH(OH) | 4-Cl-C$_6$H$_4$- | 82 |
| 15 | Cl | imidazol-1-yl | CH(OH) | 4-biphenylyl | 168 |
| 16 | F | imidazol-1-yl | CH(OH) | 4-Cl-C$_6$H$_4$- | resin |
| 17 | Cl | imidazol-1-yl | CH(OH) | -C(CH$_2$F)(CH$_3$)(CH$_2$F) | 140 |
| 18 | F | imidazol-1-yl | CH(OH) | -C(CH$_3$)(CH$_2$F)(CH$_3$) | 138–140 |
| 19 | F | imidazol-1-yl | CH(OH) | -C(CH$_2$F)(CH$_3$)(CH$_2$F) | 141 |
| 20 | Cl | imidazol-1-yl | CH(OH) | -C(CH$_3$)(CH$_2$Cl)(CH$_3$) | 132–136 |
| 21 | Cl | imidazol-1-yl | CH(OH) | -C(CH$_3$)(CH$_2$F)(CH$_3$) | 120–125 |
| 22 | F | imidazol-1-yl | CH(OH) | -C(CH$_3$)(CH$_2$-Cl)(CH$_3$) | 132 |

Use Examples

In the use examples below, the compounds indicated below are employed as comparative substances.

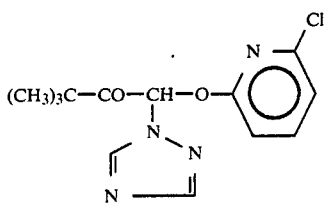

(A)

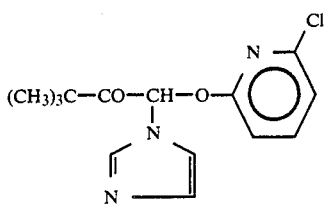

(B)

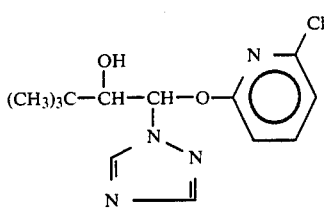

(C)

EXAMPLE A

*Leptosphaeria nodorum* test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compounds according to the following preparation examples: 1, 11, 12 and 7.

EXAMPLE B

Podosphaera test (apple)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective effectiveness young plants are sprayed with the preparation of active compound until dripping wet. After the spray coating has dried on, the plants are inoculated by dusting with conidia of the powdery mildew of apple causative organism (Podosphaera leucotricha).

The plants are then placed in a greenhouse at 23° C. and a relative atmospheric humidity of about 70%.

Evaluation is carried out 9 days after the inoculation.

In this test, a clearly superior activity compared with the prior art is shown, for example, by the compounds according to preparation examples: 1 and 2

It will be understood that the specification and examples are illustrative, but not limitative of the present invention and that other embodiments within the spirit and scope of the invention will suggest themselves to those skilled in the art.

What is claimed is:

1. An azolylalkyl pyridinyl ether of the formula

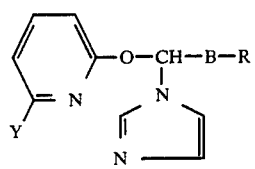

in which

Y is fluorine or chlorine,

B is a keto group or a CH(OH) group,

R is phenyl; phenyl substituted by at least one member selected from the group consisting of chlorine and phenyl;

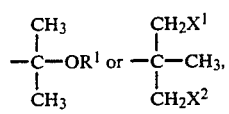

$R^1$ is phenyl, or phenyl substituted by at least one member selected from the group consisting of fluorine and chlorine, $X^1$ is fluorine or chlorine, and $X^2$ is hydrogen, fluorine or chlorine.

2. A compound as claimed in claim 1, wherein such compound is 1-(2-fluoro-pyrid-6-yl-oxy)-3-(4-chlorophenoxy)-3-methyl-1-(imidazol-1-yl)-butan-2-one of the formula

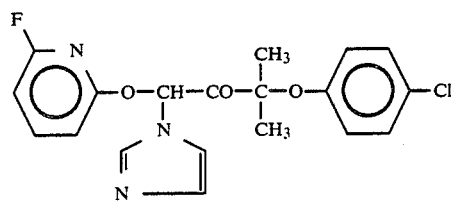

3. A compound as claimed in claim 1, wherein such compound is 1-(2-fluoropyrid-6-yloxy)-3,3-(difluoromethyl)-1-(imidazol-1-yl)-butan-2-one of the formula 4. A compound as claimed in claim 1, wherein such compound is 1-(2-chloro-pyrid-6-yl-oxy)-3-methyl-3-chloromethyl-1-(imidazol-1-yl)-butan-2-one of the formula

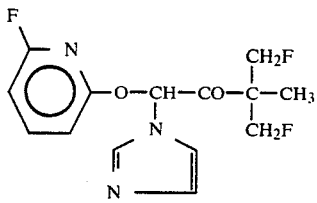

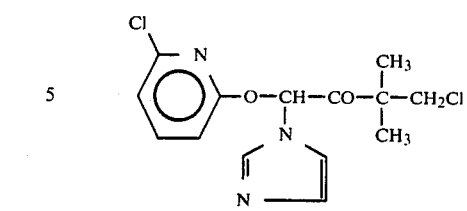

5. A fungicidal composition comprising a fungicidally effective amount of a compound as claimed in claim 1 in admixture with a diluent.

6. A composition as claimed in claim 5, containing from 0.1 to 95% by weight of the active compound.

7. A method of combating fungi, which comprises applying to the fungi or to their habitat a fungicidally effective amount of a compound as claimed in claim 1.

8. A method as claimed in claim 7, wherein the active compound is
1-(2-fluoro-pyrid-6-yloxy)-3-(4-chloro-phenoxy)-3-methyl-1-(imidazol-1-yl)-butan-2-one,
1-(2-fluoro-pyrid-6-yloxy)-3,3-(difluoromethyl)-1-(imidazol-1-yl)-butan-2-one, or
1-(2-chloro-pyrid-6-yloxy)-3-methyl-3-chloromethyl-1-(imidazol-1-yl)-butan-2-one.

* * * * *